United States Patent [19]

Smith et al.

[11] Patent Number: 4,610,744

[45] Date of Patent: Sep. 9, 1986

[54] HEAT TRANSFER PAD DECORATION AND SUBSTRATES THEREFORE

[75] Inventors: Donald R. Smith, Hingham; Mary G. Boyd, Framingham, both of Mass.

[73] Assignee: Dennison Manufacturing Company, Framingham, Mass.

[21] Appl. No.: 773,963

[22] Filed: Sep. 9, 1985

Related U.S. Application Data

[63] Continuation-in-part of Ser. No. 660,264, Oct. 15, 1984, abandoned, which is a continuation of Ser. No. 473,906, Mar. 10, 1983, abandoned, which is a continuation-in-part of Ser. No. 288,589, Jul. 30, 1981, Pat. No. 4,392,905.

[51] Int. Cl.[4] .......... B32B 31/00; B65C 9/25; C09J 5/06; A61F 13/02

[52] U.S. Cl. .......... 156/235; 156/240; 156/249; 156/330.9; 156/344; 156/320; 156/321; 156/493; 428/40; 428/914

[58] Field of Search .......... 156/230, 240, 235, 249, 156/289, 344, 320, 321, 330.9, 540, 493; 428/40, 349, 914, 352; 427/411; 106/27

[56] References Cited

U.S. PATENT DOCUMENTS

| | | | |
|---|---|---|---|
| 3,379,604 | 4/1968 | Weber et al. | 156/240 |
| 3,436,293 | 4/1969 | Newman | 156/240 |
| 3,616,176 | 10/1971 | Jachimowicz | 156/240 |
| 3,847,697 | 11/1974 | Baker et al. | 156/235 |
| 3,887,420 | 6/1975 | Weingrad | 156/240 |
| 3,899,379 | 8/1975 | Wanesky | 156/235 |
| 4,068,033 | 1/1978 | Meade | 428/914 |
| 4,211,810 | 7/1980 | Barta | 156/240 |
| 4,251,276 | 2/1981 | Ferree, Jr. et al. | 106/27 |
| 4,303,717 | 12/1981 | Andrews | 427/411 |
| 4,426,422 | 1/1984 | Daniels | 428/40 |

*Primary Examiner*—Edward Kimlin
*Assistant Examiner*—Louis Falasco
*Attorney, Agent, or Firm*—Barry D. Josephs; Arthur B. Moore; George E. Kersey

[57] ABSTRACT

A decorative laminate and method of transferring designs onto articles. The laminate is formed of a transfer substrate affixed to a support member. The transfer substrate is composed of a protective layer, an ink layer, and a nonwax-based adhesive/release layer. The adhesive/release layer is in direct contact with the support member and use of a wax layer intermediate the adhesive/release layer and the support is excluded. Optionally, a barrier layer is provided between the adhesive/release layer and the ink layer. In many applications the protective coating layer may be omitted. The laminate is applied to an article using a heated silicone rubber transfer pad to which the transfer substrate adheres during the transfer process.

10 Claims, 5 Drawing Figures

HEAT TRANSFER PAD DECORATION AND SUBSTRATES THEREFORE

BACKGROUND OF THE INVENTION

This application is a continuation in part of application Ser. No. 660,264 filed Oct. 15, 1984 now abandoned which was a continuation of application Ser. No. 473,906 filed Mar. 10, 1983 now abandoned which was a continuation in part of application Ser. No. 288,589 filed July 30, 1981 now U.S. Pat. No. 4,392,905.

1. Field of the Invention

The present invention relates to heat transfer decoration, as well as to the decoration of objects using a deformable pad. The invention further relates to the design of labels transferable by these methods.

2. Description of the Prior Art

A widely employed prior art method for imprinting designs onto articles using a heat transfer labelling process employs a paper base sheet or web coated with a label consisting of a release layer over which a design is imprinted in ink. In one successful technique of heat transfer decoration, labels of the above description are transferred to bottles or other articles using heat and pressure by feeding the article to a transfer site, where the preheated label-bearing web is impressed against the bottle to transfer the label. Patents illustrative of the above method and apparatus, commonly assigned with the present application, include U.S. Pat. Nos. 2,981,432; 3,064,714; 3,079,979; 3,208,897; 3,231,448; 3,261,734; and 4,214,937. This decorating technique, while highly successful in achieving high quality label transfer to bottles and similar articles, suffers certain limitations in achieving high quality label transfer to bottles and similar articles, suffers certain limitations in the decoration of articles of ususual shape. Since the laminate is transferred directly to the artile from a broad continuous web, the laminate lacks sufficient flexibility to conform to surfaces having compound or sharp curvature. The method is therefore not easily adaptable to imprinting objects having surfaces of compound or irregular curvature or recessed panels.

Another type of apparatus which possesses special advantages in the decoration of objects of unusual conformation is the so-called pad-transfer decorator. This apparatus utilizes a deformable pad, typically comprised of a silicone elastomer. The pad receives an ink impression to be transferred to an article by pressing against an intaglio plate which had been previously coated with ink with any excess ink removed. The impression-bearing pad is then pressed against the article to be labelled, to which it imparts the ink impression. The deformable pad is adaptable to a wide variety of article conformations. This decorative method and apparatus involves assembly-line equipment of a simpler design than the above-discussed heat-transfer decorators, and therefore requires fewer adjustments in retooling to articles of a variety of sizes and shapes. However, this process only transfers one color of ink at a time, and is thus slow and cumbersome if multicolored designs are required. Also, since there is no protective coating covering the ink design, it is left exposed directly to the environment upon transfer to the article.

U.S. Pat. No. 3,887,420 discloses the use of a silicone rubber pad to transfer designs from a decorative laminate to ceramic articles. The laminate includes a base layer such as a paper sheet overlayed with a coating of wax. The wax coating is coated with a film layer (Film B), which in turn is overcoated with an ink design layer and a second film (Film A). As the laminate is heated to within a narrow ten degree temperature range, Film A is alleged to become adhesive while the wax coating and Film B become molten and nonadhesive. The transfer pad purportedly sticks to Film A when it is pressed against the laminate so that as the transfer pad is withdrawn, the substrate composed of the paper sheet and wax coating separates from the remainder of the laminate. The laminate adhering to the transfer pad is pressed onto a ceramic article, and the temperature of the laminate is dropped to within a narrow ten degree temperature range. At this temperature, Film B becomes adhesive and Film A is alleged to exhibit diminished adhesion. Thus, as the laminate is pressed onto the article with Film B contacting the article, the laminate is alleged to adhere to the article and released from the transfer pad as the pad is withdrawn.

The film layers A and B are each adhesive over only a very narrow ten degree temperature range, making it impracticable to control the described process within the context of an automated process, since each film layer must in turn be heated or cooled to within the required ten degree temperature range to make the process workable. Precise heating or cooling of Film A and Film B to within such narrow temperature ranges is impossible to achieve or control within the split second time intervals required by an automated assembly process. This reference does not disclose the use of an independent pad heater, nor details of pad composition, surface texture, or other parameters important to its implementation. Furthermore, the inclusion of a wax layer to form part of the decorative substrate has the disadvantage that as the substrate is released from Film B there will be a strong tendency for a portion of the wax to remain attached to Film B. This will interfere with the adhesive characteristics of Film B as the laminate is transferred from the transfer pad to an object.

U.S. Pat. No. 3,616,176 discloses a heat transfer laminate of a type related to that disclosed in U.S. Pat. No. 3,616,015. In U.S. Pat. No. 3,616,176 the laminate is composed of a base sheet, with a polyamide layer covering the base sheet and a decorative ink layer covering the polyamide layer. Sufficient heat is applied to the laminate to heat the polyamide layer at or above its softening point, and the laminate is then pressed onto the surface of an article with the decorative ink layer coming into direct contact. Upon withdrawal of the heat source, the polyamide layer cools to a temperature below its softening point and the base sheet is removed. The decorative layer becomes fused or heat sealed to the article. Since the polyamide layer lies over the decorative layer, it does not contact the article directly and therefore does not function as a contact adhesive. The decorative laminate disclosed in U.S. Pat. No. 3,616,176 has a significant disadvantage that since the base sheet is in contact with the laminate as it is imprinted onto the article, the laminate lacks sufficient flexibility to satisfactorily imprint surfaces having compound or sharp curvature.

U.S. patent application Ser. No. 130,303, commonly assigned with the present patent application, discloses a heat transfer label of the type illustrated in U.S. Pat. No. 3,616,015. The heat transfer label disclosed in Ser. No. 130,303 is composed of a carrier member (base sheet) overcoated in designated regions with a release layer and an ink design layer. Optionally, a barrier layer is included between the release layer and the ink layer. The release layer is typically composed of a polymerization product of a diamine with the dimer of a fatty acid and is contoured to reduce the halo effect of the label as it is transferred onto an article. The optional barrier layer may be formed of an aromatic acid-based polyester covering and overlapping the release layer by a margin. This patent application does not suggest a solution to the above-mentioned limitations of the heat transfer labelling process.

U.S. Pat. No. 4,426,422 commonly assigned with the present patent application also discloses a heat transfer label of the type illustrated in U.S. Pat. No. 3,616,015. The heat transfer label disclosed in U.S. Pat. No. 4,426,422 is composed of a carrier member (base sheet) overcoated in designated regions with a release wax layer, a protective layer, an ink design layer, and an adhesive layer. The protective layer provides enhanced chemical resistance for the heat transfer label and permits the heat transfer process. The protective layer is typically composed of an aromatic acid-based polyester and a rosin ester. This patent appication does not suggest a solution to the above-mentioned limitations of the heat transfer labelling process.

Accordingly, it is an object of the present invention to provide decorative methods suitable for automated transfer of labels to articles, and substrates to be transferred by this method. It is a particular object of such method and apparatus that it combine the advantages of adaptability to a variety of article sizes and shapes and multicolored label capabilities.

Another object of the invention is that the technique be readily adapted to rapid and efficient operation. A related object is a multicolored decoration capability without the need for successive decorative stages.

Yet another object of the invention is the provision of a decorative process which is adaptable to a variety of articles. Such technique, for example, should be suited to the decoration of plastic, glass, and ceramic articles.

Still another object of the invention is the achievement of high quality decoration of articles. The apparatus of the invention should impart a desired image completely and without significant distortion. A particular object in this regard is the provision of high gloss images. A further object of the invention is the provision of durable, reasonably inexpensive decoration.

Another object of the invention is to provide a decorative laminate which achieves multicolor pad transfer decoration in a single transfer operation.

Another object of the invention is to provide a decorative laminate which permanently adheres to any article without subsequent firing of the laminate.

A further object of the invention is to achieve a pad transfer method which satisfies the above criteria while being compatible with automated operation.

SUMMARY OF THE INVENTION

In accomplishing the foregoing and related objects, the invention provides a transfer process employing a decorative laminate including a design and transfer substrate which are transferred from a support member to a transfer pad and thence to an article. The support member is heated to a first temperature, permitting separation of the transfer substrate which adheres to the pad. The surface of the pad is advantageously at a second, somewhat lower temperature. The transfer substrate is pressed against the article forming an adhesive bond thereto, and is released by the pad.

In the preferred embodiment, the transfer substrate includes a non-wax based adhesive/release layer which is in direct contact with the support member. The adhesive/release layer functions as a release layer permitting separation of the transfer substrate from the support as the support member is heated and as an adhesive as the transfer substrate is pressed against the article and transferred from the pad to the article. The transfer substrate of the present invention excludes use of a wax based release layer intermediate the adhesive/release layer and the support. The nonwax adhesive/release layer is softened by the heating of the support member and separated therefrom during the first transfer. This layer also functions as an adhesive forming a permanent bond to the article during the second transfer.

The transfer substrate further includes an ink design over the adhesive layer. Optionally, the substrate includes a protective coating layer over the ink layer; this layer may be omitted in many applications.

Optionally, the transfer substrate further includes a barrier layer intermediate the adhesive/release layer and the ink layer. The barrier layer, where included, functions to prevent absorption of ink into the resinous coating.

The invention has the advantage that the transfer substrate may be composed of either a single colored decorative design or a multicolored decorative design including halftone colors. Another advantage of the invention is that the transfer substrate may be transferred to virtually any type of article irrespective of its shape or degree of surface curvature without causing distortion to the design imprint. Thus, the article may, for example, be composed of ceramic, glass, plastic, paper foil, and a variety of polymeric materials, and the surface to which the transfer substrate is transposed may be flat or include compound curves, irregular surfaces, or recessed panels.

The decorative laminate of the preferred embodiment includes a paper sheet or web, which is coated on one side with the various layers constituting the transfer substrate. The transfer substrate includes a resinous coating layer in contact with the support (i.e., the adhesive/release layer), an ink layer covering the resinous coating layer and a protective coating layer over the ink layer. The use of a resinous adhesive/release layer distinguished the transfer substrate of the invention from those of the prior art incorporating a wax release layer or the like, which cannot also successfully function as an adhesive layer.

Applicants have determined that inclusion of any wax in the adhesive/release or intermediate the adhesive/release and the support or in contact with the support is undesirable because it interferes with attainment of permanent adhesion of the transferred substrate to a receiving article. Applicants have determined that exclusion of wax from the adhesive/release layer and the support has resulted in the process advantage that permits permanent adhesion of the transfer substrate to an article immediately upon transfer and without need for subjecting the transferred substrate on the article to subsequent external heat treatment (firing). In contrast, the use of a wax release layer as in Weingrad U.S. Pat. No. 3,887,420 prevents acceptable permanent adhesion of the transfer substrate to an article without subsequent firing of the transferred laminate on the article. (See Weingrad U.S. Pat. No. 3,887,420 wax release layer 30 in contact with base sheet 28 and firing of the transferred laminate at Col. 4, Lines 54–55). Applicant's present process employing a non-wax based adhesive/-release layer has the advantage of providing permanent adhesion of the transferred substrate as soon as the substrate is transferred to the article. Thus, applicant does not need to subject the transferred substrate on the article to firing, or subsequent heat treatment from external heating sources.

In the preferred embodiment, the barrier layer where included is of the same composition as the protective coating.

A preferred formulation for the adhesive/release layer is a polyamide resin made from the polymerization of a diamine with a dimer of a fatty acid. Preferably, this layer includes a plasticizer such as castor oil, which may be modified by the addition of erucamide (a fatty amide of cis-13-decosenoic acid). Particularly favorable properties are achieved in this layer when it comprises at least 80 percent by weight polyamide resin, the balance being a plasticizer.

Additional plasticizer may be included in the formulation of the adhesive/release layer to increase its fluidity. Where erucamide is included in the adhesive/-release layer the above-mentioned proportions are suitably adjusted so that the polyamide resin comprises at least 70 percent of the formulation, more preferably between 70 and 90 percent. Advantageously, in the adhesive/release layer as so modified the ration of plasticizer to erucamide is in the range 5/1 to 15/1.

The preferred polyamide range is composed of the polymerization product of a linear methylene diamine and dimerized fatty acid. Specific polyamide resins which have been found to be particularly suitable are the polymerization products of hexamethylene diamine and dimerized linoleic acid, and tetramethylene diamine and dimerized oleic acid.

Alternative constituents for the resinous coating may include polyterpenes, vinyl toluene/alpha methyl styrene copolymers and ethylene/vinyl acetate copolymers. These constituents may be used without additional additives, or plasticizers such as castor oil may be added with or without erucamide.

A preferred plasticizer is castor oil. Alternative plasticizers may include rosin esters, chlorinated paraffins, aliphatic esters, epoxy esters, alkyl aromatic phthalates, gylcol esters, and alkyl aromatic phosphates.

Applicants have found that a preferred composition for the dried protective coating and optional barrier layer consists of the combination of a polymer (i) which is a film forming, multiaromatic, acid-based polyester, preferably linear which is reinforced by a second polymer (ii) containing bulky ring structures such as polymerized rosin esters. The multiaromatic acid-based polyester (Polymer (i)) should comprise between about 50 to 80 percent by weight of the dried protective coating layer or the optional barrier layer with the polymerized rosin ester (Polymer (ii)) comprising the balance of the mixture, i.e., between about 20 to 50 percent by weight.

The multiaromatic acid-based polyester (Polymer (i)) is preferably composed of the polymer condensation products of polyester forming reactants of one or more glycols reacted with napthalic pr phthalic acids.

A preferred rosin ester (Polymer (i)) is formed typically of the reaction product of a polyhydric alcohol, maleic anhydride or phenol aldehyde reacted with rosin acids such as abietic and pimaric acids. The rosin ester (Polymer (ii)) is preferably composed of methyl abietate, methyl hydroabietate, glyceryl hydroabietate or ester gum.

The ink layer may be composed of a single colored ink or may include a multiplicity of differently colored inks. The ink may be composed of any conventional nitrocellulose ink, preferably a polyamide-nitrocellulose ink. Alternatively, inks having a acrylic polyester, or vinyl base are also particularly suitable.

If the transfer substrate does not include a protective layer, the ink layer is preferably composed of an isobutyl methacrylate ink modified with maleic rosin and polyisoprene. Alternatively, inks having a polyamide-nitrocellulose or vinyl base may be adopted if the substrate does include a protective layer.

The basis weight of the dried resinous coating layer may advantageously fall in the range 1.5 to 15 lbs./ream, and the dried protective coating layer or barrier layer from about 0.5 to 3 lbs./ream (3000 sq. ft. per ream).

In a preferred implementation of the transfer process, heat is conducted through an exposed undersurface of a support web, supplied from a heated platen or the like. Sufficient heat is supplied to tackify the protective coating layer (or ink layer, where the protective coating is omitted) and to soften and begin to melt the adhesive/-release layer. As a result, the protective coating adheres to the surface of the transfer pad, and the softened resinous coating is released from the support web. A suitable platen temperature to achieve the above objects is in the range 330° F. to 420° F., more preferably between 340° F. and 380° F., for automatic operation.

The transfer pad is heated to a surface temperature around 100° F.-200° F. lower than the platen's temperature. The heating of the transfer pad occurs as a natural result of the label pick-up process whereby the pad at least indirectly contacts the heated platen. Alternatively the pad may be fitted internally with conventional electrical heating coils to regulate the pad surface temperature to any desired level typically about 100° F. to 200° F. lower than the platen temperature. The heated pad serves to maintain the adhesive/release layer in a softened, tackified state and permits the eventual release of the transfer substrate. An illustrative temperature range is between about 50°-300° F. The various temperatures are dependent on the mechanical design of the transfer apparatus, and will tend to be lower for a given label chemistry with higher transfer pressures and lower cycle speeds.

A preferred composition for the transfer pad is an elastomeric material. Silicone rubber has the advantages of being easily molded in a variety of configurations, and having suitable deformability as known in the prior pad transfer art. In the present invention, this material enjoys the additional significant advantage of withstanding the elevated temperatures which are characteristic of the transfer process. A particular property of some importance in the transfer of smooth, glossy labels is that the pad surface have a relatively smooth texture. The pad has a convex curvature facing the transfer substrate and may take the form of a cylindrical roller.

DESCRIPTION OF THE DRAWINGS

Other aspects of the invention will become more apparent after considering several illustrative embodiments of the invention taken in conjunction with the drawings.

DETAILED DESCRIPTION

Figure 1:
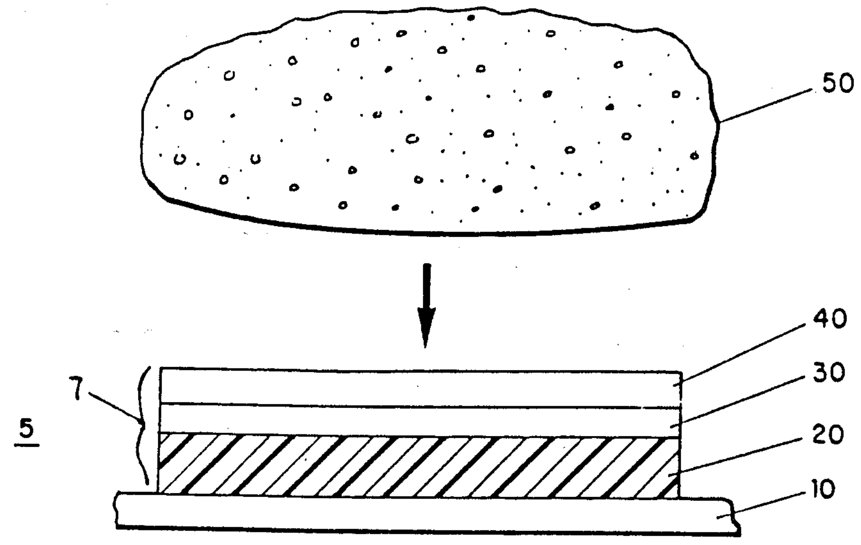
FIG. 1 is an elevated view of the decorative laminate of the invention and the transfer pad before the transfer pad is pressed onto the laminate.
Figure 2:
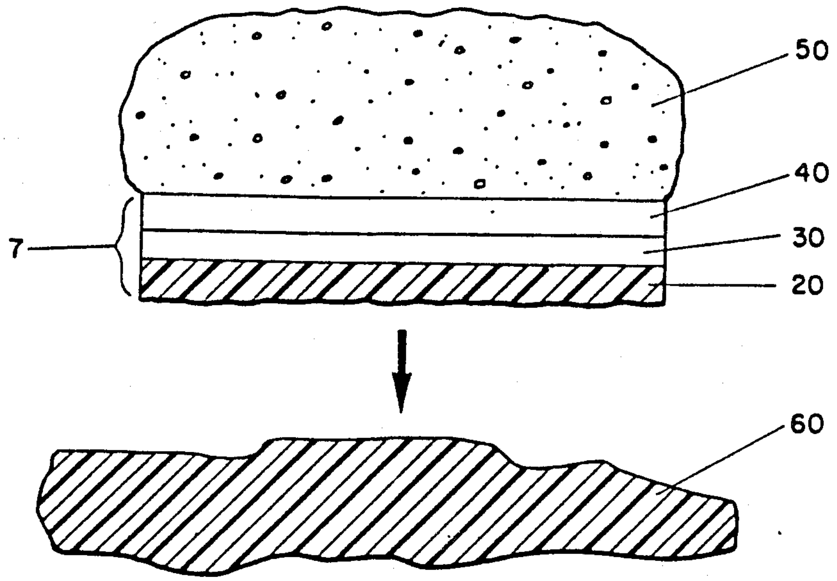
FIG. 2 is an elevated view fo the decorative laminate of the invention and the transfer pad after contact is made between the pad and the laminate and the support released.

A preferred embodiment of the decorative laminate of the invention is shown in FIG. 1. The decorative laminate 5 of the invention is composed of a support 10, typically a substrate composed of a paper sheet or web which is affixed at least on one side to a transfer substrate 7. Transfer substrate 7 as best shown in FIGS. 1 and 2, is preferably composed of a resinous coating layer 20, an ink layer 30 and a protective coating 40. Optionally, as shown in FIG. 3, the laminate 5 and substrate 7 may include a barrier layer 25 between ink layer 30 and resinous coating 20.

Laminate 5 is formed by providing support 10 with a nonwax based adhesive/release resinous coating 20 on at least one side of support 10. The transfer substrate 7 of the present invention excludes use of a wax based release layer intermediate the adhesive/release resinous coating 20 and support 10. The adhesive/release resinous coating 20 is in direct contact with support 10. Resinous coating 20 is overcoated with an ink layer 30 composed of letters or designs imprinted in ink. Ink layer 30 does not contact support 10. Ink layer 30 is then provided with an overcoating of protective coating layer 40. The transfer substrate 7 may also be provided with a resinous barrier coating between ink layer 30 and resinous coating 20.

Figure 3:
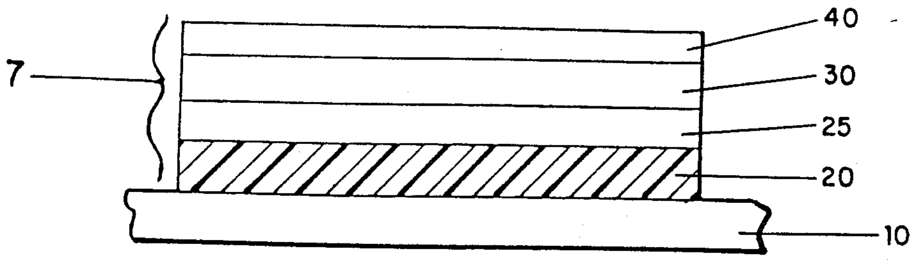
FIG. 3 is an elevated view of the decorative laminate of the invention with inclusion of a barrier layer.

The barrier coating 25 illustrated in FIG. 3 may typically be of the same composition as protective coating 40 and prevents absorption of the ink into the resinous coating 20. Use of a protective coating layer 40 is particularly advantageous when the container contents includes corrosive or abrasive elements such as alcohol, cosmetics, toiletries, food and dairy products, beverages or frozen goods.

Figure 4:
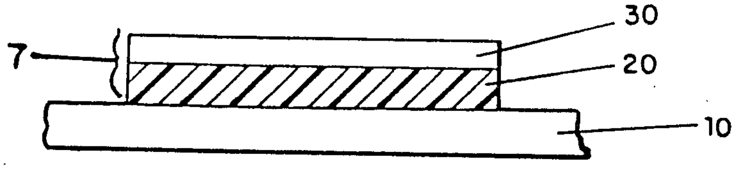
FIG. 4 is an elevated view of the decorative laminate of the invention without a protective coating layer.
Figure 5:
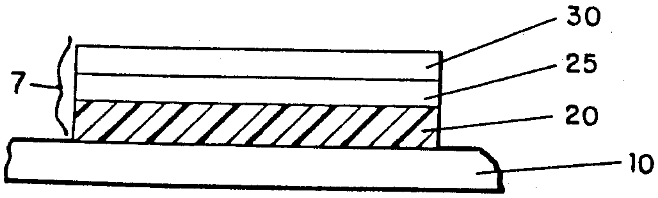
FIG. 5 is an elevated view of the decorative laminate of the invention without a protective coating layer and with inclusion of a barrier layer.

Alternatively, the protective coating layer 40 may be omitted from the transfer substrate 7 as illustrated in FIGS. 4 and 5. Protective coating layer 40 may be omitted in labelling applications, particularly wherein the transfer substrate 7 will not be exposed to harsh chemicals or corrosive elements, for example when applied to tags or containers holding chemically inactive material. In such case the transfer substrate 7 may be composed of resinous coating 20 overcoated with an ink layer 30 as illustrated in FIG. 4.

The transfer substrate 7 without a protective coating layer is affixed to support 10 as shown in FIG. 4 to form a decorative laminate 5. A barrier layer 25 may be included between ink layer 30 and resinous coating 20 to form a transfer substrate 7 as illustrated in FIG. 5 which does not have a protective coating layer. The barrier layer 25 prevents absorption of the ink into the resinous coating 20.

The laminate of the invention is particularly suitable for use in automated processes. In the process of the invention a support 10 typically in the form of a web carrying a plurality of transfer substrate 7 aligned in single rows are passed under a flexible transfer member 50, conveniently referred to as a transfer pad. The transfer pad 50, preferably composed of silicon rubber and support substrate 10 are each first heated. Transfer pad 50 is then pressed onto substrate 7 as it is passed under the pad 50 so that the pad comes into contact with the protective coating layer 40 or ink layer 30 if the substrate does not include a protective layer 40. As the transfer pad 50 is withdrawn, substrate 7 adheres to the pad and the support 10 separates from substrate 7, and substrate 7 adheres to the article. A permanent bond between resinous coating layer 20 and the article then forms. If substrate 7 includes a protective coating 40, the ink design in ink layer 30 is distinctly visible through protective coating 40 after substrate 7 has been transferred to the article. Protective coating 40 dries to a smooth, glossy finish which protects ink layer 30 from the environment.

In the first step of the process, sufficient heat is applied to the exposed surface of support 10, to heat the substrate to a temperature which is above the melting point of the resinous coating 20. Support 10 is heated to a temperature typically between about 50° F. to 150° F. above the melting point of the resinous coating 20. Typically, support 10 is heated to between about 330° F. to 420° F., more preferably 340° F.-360° F., so that the protective coating 40 (or ink layer 30, if protective coating is not included in substrate 7) becomes tacky, and resinous coating 20 softens and begins to melt enough to permit the support to be removed from transfer substrate 7. The rubber transfer pad 50, preferably composed of silicon rubber, having a smooth contact surface is heated to a temperature which is lower than the temperature to which support 10 is heated, preferably 100° to 200° F. lower than the temperature of support 10. Typically, the transfer pad 50 is heated to between about 150° F. to 300° F., more preferably 150° F.-250° F. The various disclosed temperatures are dependent on the mechanical characteristics of the transfer apparatus as well as the label chemistry and will generally be lower at higher transfer pressures and lower cycle speeds.

Transfer pad 50 will be heated as a normal incident of the transfer process, inasmuch as it will periodically, at least indirectly, contact the means for heating support 10. If this heating effect is insufficient in the context of a given system, an independent heater should be provided for pad 50.

In a second step of the process, as shown in FIG. 1, the hot transfer pad 50 is pressed against laminate 10 so as to make pressure contact with the protective coating 40 or ink layer 30 in the event protective coating 40 is omitted. The transfer pad is then withdrawn in a third step as shown in FIG. 2, at which time splits to separate from support 10 thus releasing support 10. The coating 40 or ink layer 30 is sufficiently adhesive that the substrate 7 adheres to the transfer pad. Thus, the substrate 7 is left in adhesive contact with the transfer pad 50 and resinous coating 20 is exposed to the environment.

In the fourth step of the process, the hot transfer pad 50 and adhering substrate 7 is then pressed onto a surface of either a flat or three-dimensional object including articles having compound curves, irregular surfaces, or recessed panels so that the exposed coating layer 20 comes into pressure contact with the article. The article may consist of any of a wide range of materials including ceramic, plastic, or glass.

The time interval between steps three and four is preferably less than about 1 second, more preferably between about 0.01 to 0.25 seconds. With the preferred composition for coating 20 disclosed in Table I, coating 20 will be sufficiently tacky up to temperatures from about 150° C. to 300° C.

As coating 20 comes into contact with article 60, it exhibits a tacky adhesive quality which is greater than the adhesive force between substrate 7 and transfer member 50. Transfer member 50 is withdrawn from article 60 in a fifth step of the process. The time interval between the moment of contact of substrate 7 with the article surface and the moment of withdrawal of transfer member 50 away from the article surface is preferably less than about 1 second and as low as about 0.01 second, preferably between 0.01 and 0.20 second. Thus the total time inverval as measured from the moment of withdrawal of the transfer pad 50 from support 10 to release transfer substrate 7 from support 10 until the moment of withdrawal of transfer pad 50 from the article leaving substrate 7 permanently adhered thereto is preferably between about 0.02 and 0.45 seconds. The foregoing time intervals are most readily achieved if transfer pad 50 is in the shape of a cylindrical roller. As transfer member 50 is withdrawn from article 60 substrate 7 remains in adhesive contact with the article. Coating 20 also functions to permanently bond substrate 7 to the article, almost immediately as substrate 7 is transferred to the article. Thus, the resinous coating layer 20 may be termed an "adhesive/release" layer, in that it provides the unique dual functionality as a release layer to permit separation of substrate 10 in one step of the process, and ultimately as a permanent adhesive to bond the ink layer 30 to an article. Applicant attains sufficient permanent adhesion of substrate 7 to the article without need to subject the transferred substrate 7 on the article to subsequent heat treating steps. Specifically applicant does not subject the transferred substrate 7 on the article to subsequent heat treatment from external heat sources often referred to in the art as firing.

As substrate 7 cools on the article, protective coating 40 when included in the substrate forms a hard, protective lacquer coating over ink layer 30 forming a chemical and abrasion resistant protective layer, thus sealing the ink layer from exposure to moisture vapor, oxygen, grease, and other corrosive elements in the environment. The resulting laminate has the property that the design, which may be either a single or multiple colored design, shows distinctly therethrough regardless of the type of curvature of the surface to which it has been applied and regardless of whether the article is composed of ceramic, glass, or plastic. Furthermore, the outline of the protective coating layer 40 or the resinous coating 20 on the article is essentially invisible to normal inspection.

The coating layer 20 and protective coating 40 remain permanently affixed to article 60 as an integral part of the transfer substrate. When coating 40 is not included in substrate 7, ink layer 30 is exposed directly to the environment. The affixed substrate is not subjected to firing, but it should be appreciated that if article 60 is composed of glass, an inorganic flux material may be added to form ink layer 30. In this case, if substrate 7 is exposed to high temperature firing, the organic layers 20 and 40 are volatilized leaving ink layer 30 fused to the article.

The preferred compositions of the respective layers comprising the decorative laminate 7 are set forth as follows with reference made to the accompanying tables:

Support (10)

The support 10 may be any support member or web to hold imprint substrate 7 securely attached thereto. However, it is preferable to have support 10 composed of a paper sheet more preferably a paper sheet that is clay-coated to improve its smoothness quality and to retard penetration of the resinous coating 20 into the paper sheet as heat is applied to the back of the paper. The paper sheet may be any type of paper preferably Kraft-type paper having a thickness of between about 2 to 2.5 mils and a basis weight of between about 26 to 40 lbs./ream (3000 sq. ft. ream).

Resinous Coating Layer (20)

Coating layer 20 does not contain wax and is preferably composed of a polyamide resin having a softening point advantageously between about 96° C.-105° C. The polyamide resin is preferably composed of the polymerization product of a linear methylene diamine and dimerized fatty acid. A polyamide resin which has been determined to be particularly advantageous is the polymerization products of hexamethylene diamine and dimerized linoleic acid. The formulation shown in Table I is particularly suitable for resinous coating layer 20, since it has been discovered to have the required release properties permitting the easy removal of substrate 10 in one step of the process and ultimately as a permanent adhesive to bond ink layer 30 to article 60 in another step as discussed in the foregoing.

The resinous coating layer may alternatively be composed of other materials such as polyterpenes, vinyl toluene/alpha methyl styrene copolymers and ethylene vinyl acetate copolymers.

The coating layer 20 is nonwax based, made preferably by admixing the components shown in Table I in the weight proportions by weight indicated in Table I to form a polyamide resinous solution. The mixture is prepared at ambient temperature and utilizing conventional mixing equipment.

The preferred polyamide resin shown in Table I is sold under the tradename EMEREZ 1537 by Emery Industry of Cincinnati, OH. The polyamide resin EMEREZ 1537 is the polymerization product of the type above-mentioned, namely, the product of a methylene diamine such as hexamethylenediamine and a dimerized fatty acid such as dimerized linoleic acid. It has a softening point between 110° to 120° C., a viscosity of 160° of 3.5 to 5.0 poise, a Gardner color index (max.) of 4.0, an acid value of 4.0 max., and density of 25° C. of 8.1 lbs./gal.

The resinous solution is typically prepared by dissolving the polyamide resin EMEREZ 1537 in isopropyl alcohol and toluene in the proportions indicated in Table I and then modifying the resulting solution with about 4 to 16 percent by weight castor oil plasticizer and further by the addition of 2 to 8 percent by weight of erucamide (e.g., Kenamide E). The resulting polyamide resinous dispersion has a typical preferred composition as set forth in Table I.

Erucamide is a fatty amide of cis-13-decosenoic acid sold under the tradename KENAMIDE E by Humko Sheffield Chemical Div. of Kraftco Corp., Memphis, TN.

The erucamide additive permits the use of an increased amount of castor oil plasticizer which enhances the fluidity of the resinous coating layer. The fatty amide KENAMIDE-E has an average molecular weight of 335, an iodine value between about 70 to 80, a capillary melting point of about 76° to 86° C. and a Gardner color maximum of 5.

the polyamide resinous solution having a typical composition illustrated in Table I may be applied to the support 10 by any conventional printing methods, for example, by gravure, silk screen, offset, or flexigraphic printing methods. However, the gravure method is preferred because better process print can be realized by this method as well as better economy and color consistency with long runs. After the coating is applied to substrate 10 and dried, the solvents are evaporated and the resulting dried resinous coating (20) has a typical preferred composition as shown in Table I.

The dried resinous coating (20) covering support 10 has a basis weight preferably of between about 1.5 to 15 lbs./ream, more preferably between about 3 to 5 lbs./ream (3000 sq. ft. per ream) and has a melt viscosity in the range of 3.5 to 8.5 poise at 160° C.

Ink Layer 30

Ink layer 30 may be composed of any conventional type of ink of any color including halftone colors. The inks which are preferable have the property that they do not soak into the resinous coating when applied without a barrier layer. The present invention has the advantage that multicolored inks can be used to produce a multicolored design image, that is multicolored design images transferable in one pass.

A preferred ink is a polyamide-nitrocellulose ink. In this type ink the polyamide is a dimerized fatty acid copolymerized with a linear diamine which constitutes about 80 weight percent of the ink and the remainder is essentially nitrocellulose. Alternative inks having an acrylic, polyester, or vinyl base may also be employed.

If a protective coating 40 is not included in transfer substrate 7 as illustrated in FIGS. 4 and 5, ink layer 30 is preferably composed of an isobutyl methacrylate-type ink which exhibits suitable adhesive and release characteristics to allow substrate 7 to be transferred to pad 50 and thence released therefrom as substrate 7 is pressed onto an article. A preferred ink of this type has been determined to be an ink having isobutyl methacrylate binder modified with maleic rosin and polyisoprene.

Protective Coating Layer (40)

The protective coating layer 40 has a preferred formulation shown in Table II. It is composed essentially of a film-forming, multiaromatic, acid-based polyester designated polymer (i) and a second reinforcing polymer (ii) which contains a bulky ring structure such as a polymerized rosin ester. The reinforcing polymer (ii) desirably may constitute between about 20 to 50 weight percent and preferably about 20 weight percent of the dried protective layer (40). The polymers (i) and (ii) should be soluble in the same or miscible solvents, such as toluene and methyethyl ketone. Advantageously, the polymers (i) and (ii) may have a refractive index of about 1.5.

The multiaromatic acid-based polyester (Polymer (i)) is preferably composed of the reaction products of the polymer condensation products of polyester forming reactants of one or more glycols reacted with naphthalic, or phthalic acids.

A preferred polyester polymer (i) is a linear multiaromatic acid-based polyester such as that available under the trademark VITEL PE200 from Goodyear Company of Akron, OH. The polyesters sold under the above VITEL trademark are aromatic acid-based polyesters having yellow, amorphous granules of Acid Number from 1 to 10, preferably 1 to 4, a Shore Durometer hardness of about 75 80 D, a specific gravity of about 1.25, and a ring and ball softening point of about 150° to 170° C.

A preferred reinforcing polyester polymer (ii) is a rosin ester formed typically by reaction of polyhydric alcohols, maleic anhydride or phenol aldehyde and rosin acids such as abietic and pimaric acids. The rosin ester, (Polymer (ii)) is preferably composed of methyl abietate, methyl hydroabietate, glyceryl hydroabietate, or ester gum.

A preferred reinforcing polymer (ii) of this type is sold under the trademark NEOLYN 23-75T from Hercules Chemical Company of Wilmington, Del.

A preferred protective coating layer 40 is formed of a polyester solution having the typical preferred composition set forth in Table II. The polyester resinous solution is prepared by admixing the constituents in the proportions set forth in Table II utilizing conventional mixing techniques. The polyester resinous solution is coated onto ink layer 30 by conventional printing methods such as by gravure, silk screen offset, or flexographic methods. However, the gravure method is preferred because better process print and sharper coloring can be realized by this printing method as well as better economy and color consistency with long runs.

After the coating is applied to ink layer 30 and dried, the solvents are evaporated and the resulting dried protective coating has a typical preferred composition as shown in Table II. The dried protective coating layer 40 has a basis weight preferably between about 0.5 to 3 lbs./ream (3000 sq. ft. per ream).

Additionally, the same preferred formulation above-described and as shown in Table II for the dried protective coating layer 40 may be used as an optional barrier layer 25 between ink layer 30 and the resinous coating layer 20. The method of preparing the barrier layer may also be the same as above-described for preparing the protective coating 40 by utilizing the same preferred polyester resinous solution formulation illustrated in Table II. If a barrier coating is used, the dried barrier layer between ink layer 30 and resinous coating 20 typically has a basis weight of between about 0.5 to 3 lbs./ream. Inclusion of a barrier coating is optional, but its use further protects ink layer 30 from having moisture vapor, oxygen, and grease absorbed to it through resinous coating 20.

Transfer Member 50

The transfer member 50 is preferably composed of silicone rubber. It has been found to be advantageous to provide the silicone rubber pad with a smooth surface and a convex curvature facing transfer substrate 7 so that the transfer substrate 7 has a smooth, glossy surface after it has been transferred to the article. The transfer member 50 may advantageously take the shape of a cylindrical roller. The cylindrical roller is advantageously internally heated to the aforementioned pad temperature levels discussed at page 17. When a cylindrical roller transfer member 50 is employed, the time interval between withdrawal of member 50 initially from support 10 to release transfer substrate 7 from support 10 up until contact of the transfer substrate 7 to a receiving article 60 is less than about 1 second and as low as about 0.01 second, preferably between about 0.01 and 0.2 second. Also with a cylindrical roller shaped transfer member 50 the time interval between the moment of contact of substrate 7 with the article surface and the moment of withdrawal of the cylindrical roller away from the article surface is less than about 1 second, preferably between about 0.01 and 0.2 second. Any commercially available room temperature or heat curable silicone rubber may be suitable to make the pad. For example, the pad may be formed by casting room temperature vulcanizable silicone rubber with a suitable curing agent in proportion typically of 10 parts by weight silicone rubber to 1 part by weight curing agent. A suitable room temperature vulcanizable silicone rubber can be purchased under the tradename RTV 700, and the curing agent under the tradename BETA 5, both available from General Electric Company of Pittsfield, MA. The cast silicone rubber pad product preferably has a Shore A hardness of about 4 to 35.

TABLE I

| | Percent by Weight |
|---|---|
| POLYAMIDE RESINOUS SOLUTION | |
| Polyamide Resin (e.g., EMEREZ 1537) | 25.5 |
| Solvent 1 Isopropyl Alcohol | 49.0 |
| Solvent 2 Toluene | 21.0 |
| Plasticizer Castor Oil | 3.0 |
| Erucamide (e.g., KENAMIDE E) | 1.5 |
| | 100.0 |
| DRIED RESINOUS COATING (20) | |
| Polyamide Resin (e.g. EMEREZ 1537) | 85.0 |
| Plasticizer Castor Oil | 10.0 |
| Erucamide (e.g. KENAMIDE E) | 5.0 |
| | 100.0 |

TABLE II

| | Percent by Weight |
|---|---|
| POLYESTER RESINOUS SOLUTION: | |
| Polyester Polymer (i) (e.g., VITEL PT-200 or VITEL PE-222) | 20.0 |
| Reinforcing Polyester Polymer (ii) (e.g. NEOLYN 23-75 T) | 5.0 |
| Solvent Methylethyl ketone | 75.0 |
| | 100.0 |
| DRIED PROTECTIVE LAYER (40) | |
| Polyester Polymer (i) (e.g., VITEL PE-200 or VITEL PE-222) | 80.0 |
| Polyester Polymer (ii) (e.g., NEOLYN 23-75 T) | 20.00 |
| | 100.0 |

Examples of the process of the invention and preferred method of making the product are given as follows:

EXAMPLE I

A support 10 in the form of paper web carrying a multiplicity of transfer substrates 7 aligned in single rows were passed under a silicone rubber transfer pad 50 having a smooth surface. An automatic conveyer was used to pass the transfer substrates 7 to and under the transfer pad 50. The paper web was composed of Kraft-type paper having a basis weight of between about 20 to 40 pounds per ream and the substrate 7 was made in accordance with the specification set forth in Example II. As the paper web (support 10) passed along the conveyor, the support 10 was heated to a temperature of about 350° F. At this temperature level the protective coating 40 became tacky and the resinous coating softened and began to melt.

The silicone transfer rubber pad 50 was heated to between about 200° to 250° F. As each heated substrate 7 in turn passed under hot transfer pad 50, the smooth surface of the transfer pad made pressure contact with protective coating 40 in an automatic operation. As transfer pad 50 was withdrawn, the resinous coating 20 partially separated from support 10, thus releasing substrate 7 from support 10 exposing coating 20 to the environment, with coating 40 adhered to the transfer pad.

The transfer pad 50 and adhering substrate 7 was then passed onto the surface of an article 60 which was conveyed to the vicinity of the transfer pad. Article 60 was comprised of a polyethylene, and had compound curves and irregular surfaces.

The time interval between the moment of release of substrate 7 from support 10 to the moment of contact of substrate 7 with the article was about one second.

As the transfer pad 50 was withdrawn from article 60, substrate 7 remained in adhesive contact with the article in a permanent bond between the resinous coating layer 20 and the article. The ink design in ink layer 30 was distinctly visible through protective coating 40 after substrate 7 had been transferred to the article. Upon cooling, protecting coating 40 developed a smooth, glossy finish protecting ink layer 30 from the environment. The time interval between the moment of contact of substrate 7 with article 60 and the moment of withdrawal of pad 50 away from the article was about 0.5 second.

The paper web (support 10) which was affixed with the remaining substrates 7 was conveyed automatically under transfer pad 50. As each substrate 7 in turn passed under the transfer pad, the above-described sequence was repeated to transpose a substrate 7 from the web to another article. The process was repeated automatically until all the articles on the assembly line were imprinted with a substrate 7.

EXAMPLE II

A web of support 10 composed of Kraft-type paper sheet having a basis weight of about 26 to 40 lbs./ream was fed through a gravure printer. The resinous coating (20) is formed over predesignated portions on the paper sheet by utilizing conventional gravure printing to apply the polyamide resinous solution to the paper sheet.

The polyamide resinous solution may be prepared in accordance with the formulation set forth in Table I as described in the foregoing. To facilitate the application of the resinous solution, it may be diluted further with solvent as desired preferably so that its viscosity is about 25 sec. as measured with a #4 Ford cup. As the paper web was passed through the gravure printer, a coating of the polyamide resinous solution was uniformly applied to cover predesignated portions on a side of the paper sheet.

The coated paper was then passed through a conventional convective coater dryer wherein the coating is dried at about 200° to 250° evaporating the solvents and producing a dried resinous coating layer (20) having a composition typically as shown in Table I and a basis weight of between about 1.5 to 15 lbs./ream (3000 sq. ft./ream).

The dried web was then passed in sequence through a gravure printer wherein the next layer, e.g., ink layer 30 composed of isobutylmethacrylate ink modified with maleic rosin and polyisoprene was applied over the dried resinous coating. A single ink color or multicolored inks including halftones may be applied to produce an imprint design or any number of colors. The substrate overcoated with ink layer 30 was further passed sequentially to conventional convective drying carried out at about 200° to 250° to dry the ink.

The dried substrate was then again passed through a gravure printer wherein the polyester resinous solution was applied over ink layer 30. A polyester resinous solution was then applied in accordance with the formulation set forth in Table II as described in the foregoing. However, to facilitate application of this solution by gravure imprinting, the solution was first further diluted with solvent to yield a viscosity of about 20 seconds as measured with a #4 Ford cup.

The substrate overcoated with the polyester resinous solution was dried in conventional convective coater dryers operating at about 200° to 250° until the polyester resinous solution dried to form a dried protective layer 40 having the typical preferred composition shown in Table II, and a basis weight of between about 0.5 to 3 obs./ream.

EXAMPLE III

A label-bearing web was produced as in Example II with the following modification. Prior to applying ink layer 30, the substrate overcoated with dried resinous coating 20 was passed through a gravure printer in order to apply a barrier coating 25 over ink layer 30. The barrier coating 25 was composed of the same polyester resinous solution shown in Table II. The barrier coating was dried in conventional convective coater driers at about 200° F. to 250° F., forming a barrier having typically the same composition as that of the dried protective layer 40 set forth in Table II and a basis weight between about 0.5 to 3 lbs./ream. Thus, the substrate 7 was formed of a coating layer 20, optional barrier layer 25, ink layer 30 and dried protective coating 40.

In practice, rows of individual substrates 7 may be printed onto support substrate 10 in mass production automated fashion.

EXAMPLE IV

The process of the invention was carried out in accordance with Example II and the laminate 5 and substrate 7 were manufactured as set forth in Example II except that ink layer 30 was not overcoated with protective coating 40. Instead substrate 7 was formed as illustrated in FIGS. 4 or 5 with the free surface of ink layer 30 exposed. Thus, in the process of the invention as transfer pad 50 was pressed onto substrate 7 the pad made direct contact with the exposed surface of ink layer 30 and after substrate 7 was transferred to article 60 the free surface of ink layer 30 was left exposed to the environment. In accomplishing this embodiment of the invention, ink layer 30 was formed by employing an ink formed of conventional pigment, a binder solvent, and a binder composed of a film-forming isobutyl methacrylate ink modified with maleic rosin and polyisoprene. The isobutyl methacrylate was present in the binder in an amount between about 60 to 80 percent by weight of the binder, the maleic rosin between about 15 to 25 percent by weight and the polyisoprene between about 5 to 15 percent by weight of the binder. A typical preferred binder used in forming ink layer 30 was composed of 70 parts by weight isobutyl methacrylate modified with 20 parts by weight maleic rosin and 10 parts by weight polyisoprene. The ink layer 30 was coated onto resinous coating 20 or alternatively onto barrier layer 25 and dried in the manner set forth in Example II to form the substrate 7 illustrated in FIGS. 4 and 5 respectively. The dried ink layer 30 had a basis weight of between about 0.5 to 2 lbs./ream.

It was found that the ink layer 30 in this embodiment exhibited the required adhesive characteristics to permit transfer of substrate 7 to transfer pad 50 and thence to article 60 when the process of the invention was carried out as set forth in Example I. Upon transfer of substrate 7 onto article 60, the ink design in ink layer 30 was left indelibly imprinted on article 60. Ink layer 30 exhibited abrasion and corrosion resisting properties sufficient to permit a variety of applications, particularly where article 60 contains chemically inactive and nontoxic components and where article 60 is not intended to come into contact frequently with highly abrasive materials.

Although the transfer substrate 7 is removed from substrate 10, transferred to heated pad 50 and then to the desired article within the context of an automated process in the foregoing description, it should be appreciated that other variations including manual transfer of substrate 7 are also within the scope of the present invention. The preferred substrate compositions disclosed herein admit suitable substitutions for the various components, within the scope of the adhesive/release laminate and the process for transferring this laminate to articles. The invention, therefore, is not intended to be limited to the description in the specification but only by the claims and equivalents thereof.

What is claimed is:

1. A process for transferring a decorative laminate from a support to an article, comprising the steps:

heating the laminate, which is comprised of a non-wax-based adhesive/release layer in contact with the support, and a design layer, to a first temperature above the melting point of said adhesive/-release layer, said laminate not having a wax-based release layer intermediate said adhesive/release layer and the support;

heating the surface of an elastomeric member to a second temperature below said first temperature;

contacting the laminate under pressure with the heated elastomeric member so that the laminate adheres to the elastomeric member and separates from the support upon withdrawal of said elastomeric member;

impressing the laminate against the article to bond the adhesive/release layer thereto; and withdrawing the elastomeric member from the article, whereupon the laminate remains permanently adhered to the article.

2. A process as defined in claim 1 wherein the transferred laminate on the article is not subjected subsequently to firing.

3. A process as defined in claim 1 wherein the adhesive/release layer comprises a polymerization product of a diamine with a dimerized fatty acid.

4. A process as defined in claim 1 wherein the laminate further comprises a protective layer over said design layer.

5. A process as defined in claim 1 wherein the laminate further comprises a barrier layer intermediate the adhesive/release layer and the design layer.

6. A process as defined in claim 1 wherein the first temperature is in the range 330° F.–420° F.

7. A process as defined in claim 1 wherein the second temperature is in the range from 150° F.–300° F.

8. A process as defined in claim 1 wherein the elastomeric member comprises silicone rubber having a smooth, convex surface.

9. A process for transferring a decorative laminate from a support to an article, comprising the steps:

heating the laminate, which is comprised of a non-wax-based adhesive/releaser layer in contact with the support, and a design layer, to a first temperature above the melting point of said adhesive/-release layer, said laminate not having a wax-based release layer intermediate said adhesive/release layer and the support;

heating the surface of an elastomeric member to a second temperature below said first temperature;

contacting the laminate under pressure with the heated elastomeric member so that the laminate adheres to the elastomeric member and separates from the support upon withdrawal of said elastomeric member;

impressing the laminate against the article to bond the adhesive/release layer thereto; and withdrawing the elastomeric member from the article, whereupon the laminate remains permanently adhered to the article, the time interval between contact of the laminate against the article and withdrawal of the elastomeric member from the article leaving the laminate permanently adhered to said article is in a range between about 0.01 and 0.2 seconds.

10. A process as defined in claim 9 wherein the transferred laminate on the article is not subjected subsequently to firing.

* * * * *